(12) United States Patent
Suovaniemi

(10) Patent No.: US 9,285,373 B2
(45) Date of Patent: Mar. 15, 2016

(54) METHODS AND PRODUCTS FOR DIAGNOSING AUTOIMMUNE DISEASE AND GASTRIC CANCER LINKED WITH ATROPHIC GASTRITIS

(75) Inventor: Osmo Suovaniemi, Helsinki (FI)

(73) Assignee: BIOHIT OYJ, Helsinki (FI)

( * ) Notice: Subject to any disclaimer, the term of this patent is extended or adjusted under 35 U.S.C. 154(b) by 0 days.

(21) Appl. No.: 12/799,397

(22) Filed: Apr. 23, 2010

(65) Prior Publication Data

US 2011/0104707 A1 May 5, 2011

Related U.S. Application Data

(63) Continuation of application No. PCT/FI2008/050602, filed on Oct. 27, 2008.

(60) Provisional application No. 61/000,601, filed on Oct. 26, 2007.

(51) Int. Cl.
*G01N 33/53* (2006.01)
*G01N 33/68* (2006.01)

(52) U.S. Cl.
CPC ...... *G01N 33/6893* (2013.01); *G01N 2800/062* (2013.01); *G01N 2800/24* (2013.01)

(58) Field of Classification Search
None
See application file for complete search history.

(56) References Cited

U.S. PATENT DOCUMENTS 6,872,543 B1 * 3/2005 Sipponen et al. ............ 435/7.32

FOREIGN PATENT DOCUMENTS

| WO | WO9615456 A1 | 5/1996 |
| WO | WO 02054084 A1 | 7/2002 |
| WO | WO 2005085871 | * 9/2005 |

OTHER PUBLICATIONS

Alonso et al. (J. Clin Endocr. & Metab. 2005 vol. 90, p. 5254-5258).*
Centamni et al. (Arch Intern Med 1999 vol. 159, p. 1726-1730).*
Antti I. Koivusalo, et al., "Is GastroPanel serum assay useful in the diagnosis of Helicobacter pylori infection and associated gastritis in children?", sciencedirect; Retrieved from the Internet: URL:http://www.sciencedirect.com/science/article/pii/S0732889306002458 [retrieved on Dec. 19, 2011].
Biohit: "GastroPanel—Interpretation of the Results", http://wayback.archive.org/web/, Aug. 27, 2007, Retrieved from the Internet: URL:http://web.archive.org/web/20070827103701/http://www.gastropanel.net/index.php?contentid=2 [retrieved on Dec. 19, 2011].
Biohit: "GastroPanel", www.biohit.com, 2005, Retrieved from the Internet: URL:http://www.biohit.com/resource/files/media/brochures/diagnostics/gastropanel-brochure-screen.pdf [retrieved on Dec. 19, 2011].
Checchi Serenella et al., "Serum ghrelin as a marker of atrophic body gastritis in patients with parietal cell antibodies", Journal of Clinical Endocrinology & Metabolism, vol. 92, No. 11, Aug. 21, 2007, pp. 4346-4351, XP002606746, ISSN: 0021-972X.
European Office Action dated Jan. 26, 2012 issued in corresponding application No. 08 842 047.6.
Koivusalo A I et al., "Is GastroPanel serum assay useful in the diagnosis of Helicobacter pylori infection and associated gastritis in children?", Diagnostic Microbiology and Infectious Disease 200701 US LNKD-DOI:10.1016/J.DIAGMICROBIO.2006.06.022, vol. 57, No. 1, Jan. 2007, pp. 35-38, ISSN: 0732-8893.
European Search Report dated Nov. 9, 2010 issued in Application No. 08 84 2047.
Junca Jordi et al: "The relationship between idiopathic thrombocytopenic purpura and pernicious anemia" British Journal of Haematology, 2000, pp. 513-516.
Kazimierz Rembiasz et al: "Biomarkers in various types of atrophic gastritis and their diagnostic usefulness" Digestive Diseases and Sciences, Kluwer Academic Publishers—Plenum Publishers, NE LNKD-DOI:10, vol. 50, 2005, pp. 474-482.
Presotto Fabio et al: Helicobacter pylori infection and gastric autoimmune diseases: Is there a link, Helicobacter, 2003, vol. 8, pp. 578-584.
Segni Maria et al: "Early manifestations of gastric autoimmunity in patients with juvenile autoimmune thyroid diseases" Journal of Clinical Endocrinology & Metabolism, 2004., vol. 89, pp. 4944-4948.
Checci, S. et al. Serum ghrelin as a marker of atrophic body gastritis . . . J. Endocrin. &Metabolism Nov. 2007 vol. 92 nr 11 pp. 4346-4351.
Sipponen, P. et al. Atrofisen gastriitin toteaminen verinaytteesta. Suomen Laakarilehti, 2001, vol. 56, Nr 38 pp. 3833-3839.
Vaananen H et al. Non-endoscopic diagnosis of artophic gastritis . . . Eur. J. of Gastroenterlogy & Hepatology, 2003, vol. 15, nr 8 pp. 885-891.
Floreani A et al. Chronic atrophic gastritis and Helicobacter pylori infection . . . J. Gastroenterology and Hepatology, Feb. 1997 vol. 29, nr. 1 pp. 13-17.
Annibale B et al. Role of Helicobacer pylori infection in pernicious anemia. Digestive and Liver Disease, 2000, vol. 32, nr. 9 pp. 765-762.

* cited by examiner

*Primary Examiner* — Jacob Cheu
(74) *Attorney, Agent, or Firm* — Sughrue Mion, PLLC

(57) ABSTRACT

The present invention relates to a method for examining a person having symptoms and/or biomarkers indicating an autoimmune disease for the presence of atrophic gastritis. The biomarker combination, which diagnoses atrophic gastritis, acts also as a part of a biomarker panel that helps diagnosis and assessment of autoimmune disease as well. The invention relates also to products used in these methods.

12 Claims, No Drawings

METHODS AND PRODUCTS FOR DIAGNOSING AUTOIMMUNE DISEASE AND GASTRIC CANCER LINKED WITH ATROPHIC GASTRITIS

PRIORITY

This application is a Continuation of International Application No. PCT/FI2008/050602, filed Oct. 27, 2008, which claims the benefit of U.S. Provisional Application No. 61/000,601, filed Oct. 26, 2007.

FIELD OF THE INVENTION

The present invention relates to methods and products for examining a person having the symptoms and/or biomarkers indicating an autoimmune disease and/or atrophic gastritis.

Patients with most autoimmune diseases are at increased risk of atrophic gastritis of the stomach mucosa, which carries with it an increased risk of stomach cancer and some other diseases, such as the diseases related to the deficiency of vitamin B12, zinc, iron and calcium, and an accompanying *Helicobacter pylori* (*H. pylori*) infection.

Atrophic gastritis is a chronic gastritis that affects the corporal mucosa. It is characterized histologically by chronic inflammation of the gastric mucosa with loss of glandular cells and replacement by intestinal-type epithelium and fibrous tissue. Clinically, it is characterized by hypo- or achlorhydria and loss of intrinsic factor resulting in pernicious anemia. The immunological biomarker of pernicious anemia that is currently used is the presence of autoantibodies to gastric parietal cells (AGPA), parietal cell antigen H,K-ATPase and intrinsic factor. Only about 65% of patients with gastritis and *H. pylori* infection are AGPA positive. Normal subjects exhibit an age related increase in the incidence of AGPA from 2 to 8%. Consequently, AGPA is not sensitive and specific enough for the diagnosis of atrophic gastritis and related risks, such as gastric cancer, and related possible autoimmune diseases.

The causes of autoimmune diseases are still obscure: Some are thought to be either examples of, or precipitated by, diseases caused by affluence. For example, arthritis and obesity are known to be related, and the World Health Organisation states that arthritis is most common in developed countries. Most autoimmune diseases are probably the result of multiple circumstances, for example, a genetic predisposition triggered by an infection. Diseases with a complete autoimmune etiology include acute disseminated encephalomyelitis, Addison's disease, ankylosing spondylitis, antiphospholipid antibody syndrome, diabetes mellitus type 1, Goodpasture's syndrome, Graves' disease, Guillain-Barre syndrome, Hashimoto's disease, idiopathic throbocytopenic purpura, lupus erythematosus, multiple sclerosis, myasthenia gravis, pemphicus, rheumatoid arthritis, Sjögren's syndrome and temporal arteritis. Diseases with a complete or partial autoimmune etiology are, for example, aplastic anemia, autoimmune hepatitis, autoimmune oophororsi, celiac disease, Crohn's disease, gestational pemphicoil, Kawasaki's disease, Opsoclonus myoclonus syndrome, optic neuritis, Ord's thyroiditis, pernicious anemia, primary biliary cirrhosis, Reiter's syndrome, Takauasu's arteritis, warm autoimmune hemolytic anemia and Wegener's granulomatosus. Preferably, the list also includes dermatological pathologies, such as vitiligo.

Most of these autoimmune diseases may present with atrophic gastritis of the stomach mucosa with a high risk of stomach cancer and some other diseases, such as *Helocobacter pylori* and the diseases related to the deficiency of vitamin B12, zinc, iron and calcium.

Autoimmunity is a complex phenomenon possibly involving biologically different organs. This means that in same patient it is possible to find, besides thyroid autoimmunity, for example celiac disease, diabetes, dermatological pathologies, such as vitiligo, and of course atrophic body gastritis.

Consequently, there is need for a reliable diagnosis and screening method for revealing atrophic gastritis in people with symptomatic or asymptomatic autoimmune disease.

SUMMARY OF THE INVENTION

An aim of the present invention is to solve at least some problems of the prior art. In particular, it is an aim of the present invention to provide a method for examining a person having symptomatic or asymptomatic autoimmune disease. Furthermore, it is an aim of the present invention to provide method for examining a person having the symptoms and/or biomarkers indicating atrophic gastritis. It is also an aim of the present invention to provide products for use in these methods.

One object of the present invention is thus to provide a method for examining a person having the symptoms and/or biomarkers indicating an autoimmune disease. More specifically, an object of the present invention is to provide a method for examining a person having the symptoms and/or biomarkers indicating an autoimmune disease for the presence of atrophic gastritis. The method comprises the measuring of at least one of the biomarkers indicating atrophic gastritis. Preferably, the biomarkers are selected from the groups of biomarkers comprising 1) pepsinogen I, pepsinogen II, pepsinogen I/II ratio, gastrin-17 and *Helicobacter pylori* antibodies, 2) pepsinogen I, pepsinogen II, pepsinogen I/II ratio, gastrin-17, 3) pepsinogen I, pepsinogen II, pepsinogen I/II ratio *Helicobacter pylori* antibodies, 4) pepsinogen I, pepsinogen II, pepsinogen I/II ratio, and 5) pepsinogen I.

Another object of the present invention is to provide a method for examining a person having the symptoms and/or biomarkers indicating atrophic gastritis for the presence of one or several autoimmune diseases. The method comprises that the person is examined for the presence of the symptoms and/or biomarkers indicative of one or several autoimmune diseases.

The invention provides also a combination of biomarkers for studying a biological sample comprising one or several biomarkers of one or several autoimmune diseases, and one or several biomarkers indicative of atrophic gastritis. The biomarkers indicative for atrophic gastritis are preferably selected from the groups of biomarkers comprising 1) pepsinogen I, pepsinogen II, pepsinogen I/II ratio, gastrin-17 and *Helicobacter pylori* antibodies, 2) pepsinogen I, pepsinogen II, pepsinogen I/II ratio, gastrin-17, 3) pepsinogen I, pepsinogen II, pepsinogen I/II ratio, *Helicobacter pylori* antibodies, 4) pepsinogen I, pepsinogen II, pepsinogen I/II ratio, and 5) pepsinogen I.

In an embodiment of the invention, the reference range for pepsinogen I value is 30-160 µg/l, for pepsinogen II 3-20 µg/l, for Pepsinogen I/II ratio 3 or below 3, for Gastrin-17S (stimulated) value 5-30 µmol/l, for Gastrin-17B (fast) 2-10 pmol/l and the reference range for HPAB 0-30 EIU.

Typical cut-off values for the biomarkers are selected from the group comprising: pepsinogen I 30 µg/l, PepsinogenI/II ratio 3, Gastrin-17S (stimulated) value 5 pmol/l, Gastrin-17B (fast) 2 pmol/l and HPAB 30 EIU.

In addition, the biomarker combination (the panel), which reveals atrophic gastritis, may also be a biomarker for one autoimmune disease or several autoimmune diseases.

The whole panel could be used on patients with previously unknown autoimmune status; or in patients, who are known to have autoimmune disease, but in whom biomarkers for other autoimmune conditions as well as atrophic gastritis should be checked.

The method according to the invention is mainly characterized in that, what is stated in claim 1.

The biomarker according to the invention is mainly characterized in that, what is stated in claim 10 and a combination of biomarkers is mainly characterized in that, what is stated in claim 11.

DETAILED DESCRIPTION OF THE INVENTION

An inverse relationship is present between atrophic gastritis, particularly corpus atrophic gastritis, and the number of autoimmune diseases in the same subject. It has surprisingly been found that, when only one autoimmune disease is found in the patients, about 15% of the subjects experience atrophic gastritis, opposite to about 20% in the group having at least 2 autoimmune diseases, and about 50% in the group showing the presence of three or more autoimmune disorders.

Thus, autoimmunity plays a crucial role in determining the damage in the body (corpus) of the stomach.

GastroPanel® and GastroView™ Innovation.

Australian doctors Barry J. Marshall and J. Robin Warren received the Nobel Prize for the discovery of *Helicobacter pylori*, and for elucidation of the role of this novel bacterium in gastritis and peptic ulcer diseases (1,2). The GastroPanel® innovation allows practising physicians to benefit from these significant findings better than before (3-5). These two discoveries together promote the development of safe, ethical and cost effective evidence-based and preventative medicine.

With *H. pylori* discovered as a cause of gastritis, publications of the Finnish Gastritis Research Group, Professors Max Siurala and Pentti Sipponen, and co-workers, on chronic gastritis and atrophic gastritis from the 70's and 80's helped Professors Marshall and Warren to realize that the infection and gastritis are connected to development of ulcer diseases and stomach cancer. This research work of the Finnish physicians, but also the Italian research group leaded by Professor Fransesco DiMario, has links to the understanding of the injurious effect of *H. pylori* on gastric mucosa, and forms the backbone of the GastroPanel® examination (6-13).

Consequently, the GastroPanel® examination is based on the Finnish research tradition into chronic gastritis and associated gastric diseases on co-work with Professor Michael Samloff (11) and on Professor Osmo Suovaniemi's innovations, which have affected to the microplate analyses worldwide and have been utilized quite extensively and successfully since the 70's. His innovations also resulted, among other things, in the rapid and massive development of reliable and safe non-radioactive microplate immunoassays, on which the GastroPanel® ELISA-tests are based (14).

GastroPanel® Biomarkers.

Based on the comparative studies by the gastroscopy and biopsy specimen examinations, the biomarker tests of the GastroPanel® innovation, pepsinogen I and II (PGI, PGII), gastrin-17 (G-17) and *H. pylori* IgA&igG antibodies, have been validated to complement each other so as to form a diagnostic panel. *H. pylori* IgA & IgG antibodies are a marker of *H. pylori* infection; the level of PGI and the ratio PGI/PGII are markers of the function and structure of corpus mucosa; and the level of G-17, which is usually measured in a fasting blood sample, is a marker the function and structure of antrum mucosa. The GastroSoft computer program is used in interpretation of the GasroPanel® results. To obtain full benefit it is important to note that the GastroPanel® biomarkers (PG I, PG II; G-17 and *H. pylori* IgA & IgG antibodies) are assayed from the same blood (plasma) sample as a panel, with the optional application of GastroSoft to aid interpretation of the results (3). GastroPanel® examination is intended for safe, ethical and cost effective diagnosis and screening of dyspepsia, *H. pylori* infection and atrophic gastritis and related risks (12-23). These risks include gastric cancer, peptic ulcer disease and the deficiency of vitamin B12, iron, zinc and calcium. GastroPanel® also aids in the assessment of the development of gastroesophageal reflux disease (GERD) and its complications, such as erosive esophagitis and Barrett's esophagus, which may lead to esophageal cancer. Gastro-Panel® is suitable for diagnosis of atrophic gastritis as well as for indication of the cause of atrophic gastritis. If the patient diagnosed with atrophic gastritis based on PGI, PGI/PGII and G-17 levels does not have, and has not had, *H. pylori* infection (*H. pylori* IgA & IgG antibody test and patient history), atrophic gastritis is very likely caused by autoimmune disease.

GastroView™ Biomarkers.

It is known that the assay of *H. pylori* infection alone does not diagnose atrophic gastritis of the stomach mucosa, and, in addition, some *H. pylori* tests are not reliable (see Table). The GastroView™ examination (*H. pylori* IgA&IgG antibodies and PG I and PGII) provides a reliable diagnosis of *H. pylori* infection and the concentration of PG I and PG II in serum or plasma (4,5). This is not sufficient to provide information on the function and structure of the whole stomach mucosa. This is because the PG I level and PGI/PG II ratio only reveal atrophic gastritis of the gastric corpus, not that of the gastric antrum. However, the normal results of the round-the-clock GastroView™ examination from a non-fasting blood (plasma) sample are sufficient to reveal that the stomach mucosa is healthy (not *H. pylori* infection nor atrophic gastritis). If the results are not normal, it is a strong indication for the confirmation and further examination by the Gastro-Panel® examination from a fasting blood (plasma or serum) sample.

The assessment of the function and structure of antrum mucosa by the GastroPanel® examination is extremely important because atrophic gastritis starts in most cases from the distal stomach (the antrum and its angulus), from which it may extend upwards to the corpus. Low G-17 and *H. pylori* IgA&IgG antibodies are biomarkers of atrophic gastritis of the antrum. The patients with *H. pylori* infection and low G-17 either have atrophic antral gastritis, and/or so called antral predominant gastritis characterized by high acid output and high risk of peptic ulcer disease. These patients should undergo gastroscopy and biopsy sample examinations due to an increased risk of the precancerous lesions or early cancer in the antrum. Such patients may also be at increased risk of the occurrence of GERD and its complications.

Antrum Atrophy and High Acid Secretion.

GastroPanel® tests are usually done on a fasting plasma sample (24). If a patient with *H. pylori* infection and low G-17 does not want to have invasive gastroscopy, atrophic gastritis of the antrum can be confirmed or excluded by assaying the concentration of protein-stimulated G-17 in plasma in addition to a fasting GastroPanel® examination. In case of antrum atrophy, the fasting level of G-17 is low due to the absence of the G-cells and the protein stimulation cannot increase the G-17 level. Gastric acid in turn inhibits the secretion of G-17, and in cases with high intragastric acidity alone, protein stimulation clearly raises the plasma level of G-17 (the G cell population in antrum is normal). It is thus possible to distinguish the patients with atrophic gastritis in the antrum from those whose low fasting concentration of G-17 is entirely due to high acid secretion. If the antrum is not atrophied, protein stimulation increases the level of G-17 in the blood to over 5.0 pmol/l. If the protein-stimulated G-17 concentration is less than 5.0 pmol/l and the patient has a *H. pylori* infection, it is very likely that the patient has atrophic gastritis of the antrum mucosa.

The relation between low G-17, antrum atrophy and high acid secretion is explained by the well known physiological feedback mechanism between antrum and corpus. Patients without *H. pylori* infection and with G-17 fasting values of less than 2.0 pmol/l, who have increased G-17 levels following protein stimulation, may be at risk of the severe complications (erosive esophagitis and Barrett's esophagus) of gastroesophageal reflux disease (GERD). This risk is significantly more likely if the fasting level of G-17 is 1.0 pmol/l or lower. PG I is normal or high in these patients (19).

The detection of G-17 and subsequent early diagnosis of atrophic gastritis of the antrum provides possibilities to find patients at significant risk for gastric cancer in the gastric antrum, and offers tools to delineate subjects at particular risk for peptic ulcer diseases. It is also important that the diagnosis of atrophic gastritis, limited to gastric corpus (low PGI and low PG I/PG II), is confirmed by the high G-17. This is due to the physiological feedback mechanism between the corpus and antrum, where lack of PGI and the consequent lack of acid secretion results in increase of G-17 production and secretion. On the other hand, low plasma level of G-17 with low PGI (and/or low PGI/PGII ratio) enable to delineate patients at highest risk for gastric cancer; i.e., those with extended and severe atrophic gastritis in both antrum and corpus. These and some other facts below demonstrate how extremely important is the use of the validated combination of PG I and PG II with G-17 and *H. pylori* IgA&IgG antibodies (The GastroPanel® innovation).

Gastrin-17 and the Risk of Gastric Cancer and Peptic Ulcer Disease.

A person with moderate or severe atrophic gastritis in the antrum (low G-17 and *H. pylori* IgA&IgG antibodies) has an 18 times higher risk for stomach cancer than a healthy person. A person with moderate or severe atrophic gastritis in the corpus (low PG I and/or low PG I/PG II and high G-17) has "only" 5 times higher risk to have stomach cancer than a healthy person. If both the corpus and antrum have moderate or severe atrophic gastritis, the risk of cancer is 90 times higher (10). This information, among other things, helps to realize how extremely important (safe, ethical and cost effective; lege antis) it is to test G-17 due to the risk of gastric cancer.

G-17 is also a biomarker for the risk of peptic ulcer disease. Bleeding peptic ulcers, which are severe complications of peptic ulcer disease and increasingly due to the use of NSAID medication, are killing 200-300 people/year in Finland (the population 5.2 million). To compare, some 400-600 people die annually from advanced gastric cancer. Proper diagnosis of people at risk of peptic ulcer disease by GastroPanel® would save people from unnecessary complications, and even from death. In addition, it is conceivable that screening of people at age over 45 in Finland with GastroPanel® would save 250-300 people annually from unnecessary death due to gastric cancer (patients could be found at a curable stage) (11).

Asymptomatic GERD and NERD vs. ERD.

GastroPanel® examination also identifies asymptomatic patients (approx. one third of GERD patients) who are at risk of GERD's complications, and improves the accuracy of diagnostics in GERD patients. Among GERD patients with heartburn symptoms, NERD (non-erosive reflux disease) is likely if the levels of GastroPanel® biomarkers, including G-17, are normal. ERD (erosive reflux disease) in turn is likely if GastroPanel® is normal except for low G-17 level (<1 pmol/l). PG I level may or may not be high (over 165 µg/l). ERD is a serious disease and requires effective proton pump inhibitor (PPI) therapy. In some cases, ERD may develop into Barrett's esophagus and even to esophageal cancer. Some authors have started to promote GastroPanel® for the differential diagnosis of NERD and ERD (Gut 2006; 55 suppl VA 267).

GastroPanel® Examination Before PPI Medication.

GastroPanel® examination is applicable and useful to be used prior to the PPI medication, to ensure that the patient does not have atrophic gastritis and hypochlorhydric or even achlorhydric stomach. In addition, PPI treatment can alleviate, and therefore mask, symptoms of serious diseases such as gastric cancer and bleeding peptic ulcer, and may thereby delay the proper diagnosis and treatment.

Hypochlorhydria Due to Corpus Atrophy and PPIs.

Hypochlorhydria caused by corpus atrophy and PPIs also makes the person susceptible to the colonization of the stomach with microbes from oral cavity or from lower gut. In consumption of carbohydrates, which form part of most balanced meals, the colonized oral bacteria can elicit the production of carcinogenic acetaldehyde by fermentation in the stomach. Hypochlorhydria of the stomach is associated with a strongly increased risk of gastric cancer (26-27). The decreased intestinal absorption of calcium due to atrophic gastritis and long-term PPI therapy predisposed to a risk for, e.g., osteoporosis and hip fractures (28). In addition, hypochlorhydric states, such as atrophic gastritis and partial gastrectomy, have long been known to be causes of iron deficiency anemia (29).

Deficiency of vitamin B12.

Undiagnosed atrophic gastritis often leads to vitamin B12 deficiency, which appears to affect up to 10% of the elderly population (18). Vitamin B12 deficiency is considered to be associated with development of dementia, depression and peripheral neuropathies. In all tissues and cells, it increases in the concentrations of homocysteine that is considered an independent risk factor for atherosclerosis, heart attacks and strokes. Vitamin B12 deficiency and its causes are reversible if detected and treated early, but, unfortunately, this is rarely the case.

GastroPanel® Summary.

When GastroPanel® indicates the gastric mucosa is healthy, the dyspepsia symptoms are often caused by functional dyspepsia or another disease not involving the gastric mucosa. GastroPanel® can be used to differentiate the patients who really need gastroscopy from those who do not need it urgently. In this way it is possible to save and rationalize limited endoscopy resources for more important purposes. As much as 50% of dyspepsia symptoms may be of colon origin, especially in elderly population.

In addition, by considering that patients with atrophic gastritis and related risks (gastric cancer, peptic ulcer disease and the deficiency of vitamin B12, iron, zinc and calcium) are often asymptomatic, GastroPanel® screening of the whole population over 45 years of age would help to find the individuals who require gastroscopy. This may be carried out with little or no significant change in total number of gastroscopies needed compared to the current situation, but it would result in a significant improvement in the early detection and treatment of serious disease. In addition to diagnosing *H. pylori* and atrophic gastritis, GastroPanel® results can be used in assessment the patient's suitability and need for PPI treatment and the risk of complications of GERD.

Replacement of *H. pylori* $^{13}$C-Urea Breath Test and Stool Antigen Test with GastroPanel®.

The above presented facts emphasize why dyspepsia and *H. pylori* patients should not be tested by the $^{13}$C-urea breath test or stool antigen test, even though they are included in the current "test and treat" strategy. They only detect *H. pylori* infection but nothing else, and can be unreliable even in the proper diagnosis of the on-going *H. pylori* detection (see Table and Strategies 1-5). The $^{13}$C-urea breath test and stool antigen test give 40-50% false negative results if the patient has atrophic gastritis; MALT lymphoma; or bleeding peptic ulcer disease; or if the patient has currently received antibiotics or PPIs (30-36). These are cases where the reliable *H. pylori* detection and treatment would be especially important. *H. pylori* IgA & IgG antibody test combination does not have these types of false negative results.

In addition, there is another reason for using the *H. pylori* IgA & IgG antibody test combination of GastroPanel® examination for *H. pylori* detection (37,38): "Nearly all infected individuals (>90%) exhibit *H. pylori*-specific IgG antibodies. Most (approximately 70%) of these individuals also exhibit IgA antibodies. Approximately 7% of infected individuals are positive for IgA antibodies but negative for IgG antibodies; the reason for this aberrant response remains unclear."

By referring to his own studies and the scientific literature Professor Pasechnikov et al conclude the following (16): "The analysis of the literature data and results of our own research allow us to conclude that the serious medical and ethical problems of the "test and treat" strategy can be corrected simply and economically by replacing its $^{13}$C-urea breath—or stool antigen test by the GastroPanel® examination. Talley et al. (2004) indicate that in many countries, such as Sweden and the US, the "test and treat" strategy alone is not considered sufficient (39). The *H. pylori* tests of the "test and treat" strategy does not find atrophic gastritis and related risks, such as gastric cancer and precancerous lesions, which should be confirmed by gastroscopy and biopsy specimen examination and would be successfully treated. Consequently, GastroPanel® & gastroscopy and biopsy specimen examinations reveal patients with precancerous lesions and early stage gastric cancers, and, therefore, save people from unnecessary deaths because of gastric cancer." (see Table and Strategies 1-5).

GastroPanel® Helps to Avoid Malpractice and its Consequences.

The use of $^{13}$C-urea breath test or stool antigen test delays correct diagnoses and treatments and may lead to malpractice and even unnecessary deaths due to, for example, misdiagnosed gastric cancer and bleeding peptic ulcers. In addition, the use of inaccurate and even misleading tests causes unnecessary costs for healthcare, social security, insurance companies, employers, and for patients themselves. Now, when the GastroPanel® examination is available, it is reasonable and ethical to give up the old tests ($^{13}$C-urea breach test or stool antigen test) in the diagnosis and treatment of the patients with dyspepsia, *H. pylori* infection and atrophic gastritis with related risks (gastric cancer, peptic ulcer disease and the deficiency of vitamin B12, iron, zinc and calcium).

Opinion leaders, laboratories and doctors have an unquestionable authority and responsibility to recommend, offer and use the best possible examination and treatments that are available. Today, there are only two available options in proper and comprehensive, safe and ethical examination of the stomach mucosa. These are: 1) gastroscopy and histological examination of biopsy samples and 2) GastroPanel® examination.

GastroPanel® examination is particularly preferred in primary care and health screening especially if the endoscopic resources are insufficient. When comparing GastroPanel® and gastroscopy, accurate diagnosis cannot always be made from a few biopsy specimens. In patients with atrophic gastritis, positive serology (*H. pylori* IgA&IgG antibodies) results may indicate an ongoing *H. pylori* infection in spite of negative $^{13}$C-urea breach test and histology results (33-36). In addition, the histological diagnoses of two pathologists may diverge. The quality of histology is strongly dependent on experience and competence of the gastroenterologist and pathologist.

GastroPanel® is not associated with such problems since the biomarkers determined in blood give objective information on the function and structure of the stomach mucosa irrespective of the person examining them. If there are alarming changes in these biomarkers, the GastroPanel® examination must be followed by a careful gastroscopy. In such a case, the information provided by GastroPanel® is very helpful (22, 40). The GastroPanel® examination prevents unnecessary gastroscopies and helps target the use of sparse endoscopic resources appropriately, particularly for the screening of colorectal cancer. The dyspeptic patients age 50 or over, whose stomach mucosa is found to be healthy, should be referred for a colonoscopy, as almost half of stomach pains and disorders may be colon-related.

In medicine, it is obvious that good diagnostics go hand-in-hand with proper treatment. The business world as well as Food and Drug Administration (FDA) regulators are increasingly building this understanding into product development by supporting co-development of new drugs with development of diagnostics. This new development and the combination of the GastroPanel® diagnostics with the PPI treatment of GERD as well as with the antibiotics and PPI treatment of *H. pylori* infection would promote the safe, ethical and cost effective evidence based and preventative medicine.

GastroPanel® examination should be required by the authorities before the reimbursement of the costs of any PPI treatment of GERD. In addition, a reliable diagnosis of *H. pylori* infection with related risks made by the GastroPanel® examination or professionally performed gastroscopy and biopsy specimen examination (gastroscopy) should be the basis for the reimbursement of the costs of the *H. pylori* eradication treatment.

This guidance and contribution, for the development of the safe, ethical and cost effective evidence based and preventative medicine, will substantially reduce the costs of health care as well as prevent diseases, promote wellbeing and even save unnecessary deaths, for example, due to gastric cancer and bleeding peptic ulcers.

Gastroscopy has been the only method employed for the safe screening and diagnosis of dyspepsia, atrophic gastritis and gastric cancer, which is the second most common cause of cancer-related deaths worldwide. After evaluating the risk of atrophic gastritis and gastric cancer with GastroPanel® tests, researchers have concluded that serum pepsinogens, gastrin-17 and *Helicobacter pylori* antibodies can be employed effectually to screen for dyspepsia, atrophic gastritis and gastric cancer (11, 13-16, 21-23, 41, 42).

Screening of atrophic gastritis and related risks (gastric cancer, peptic ulcer disease, the deficiency of vitamin B 12, iron, zinc and calcium) is now considered the standard of care for persons age 45 and older. Its omission might be a frequent source of litigations due to malpractice, what it has been considered to be in a case of the omission of colorectal cancer screening for persons age 50 or over (43).

In order to avoid malpractice and save people from, e.g., unnecessary deaths because of gastric cancer the serious medical and ethical problems of the "test and treat" strategy should be corrected simply and economically by replacing its $^{13}$C-urea breath test or stool antigen test by the GastroPanel® examination (16).

Table 1. Summary of the data provided by the GastroPanel® examination and the $^{13}$C-urea breath—or stool antigen test of the "test and treat" strategy. The GastroSoft program supplies a patient report. The reports produced by GastroSoft are based on clinical studies comparing the results of GastroPanel® examinations with results from gastroscopy and biopsy examinations (www.biohit.com/gastrosoft).

The serious medical and ethical problems of the "test and treat" strategy can be corrected simply and economically by replacing its $^{13}$C-urea breath test or stool antigen test by the GastroView™ round-the-clock examination (www.gastroview.com, www.gastroprofile.com) or GastroPanel® examination (www.gastropanel.net, www.biohit.com/Diagnostics/Literature).

| GastroPanel® | The GastroSoft report states: | $^{13}$C-urea breath test or Stool antigen test report: |
|---|---|---|
| The diagnosis for | | |
| Functional vs. organic dyspepsia. When GastroPanel® indicates the gastric mucosa is healthy, the dyspepsia complaints are often caused by functional dyspepsia or another disease not involving the gastric mucosa | YES | NO |
| H. pylori infection (gastritis) | YES | NOT RELIABLE (1) |
| Atrophic gastritis (damaged and severely dysfunctional gastric mucosa of the corpus or antrum or both) | YES | NO |
| The risks (due to atrophic gastritis) of | | |
| Gastric cancer (in antrum and/or corpus) | YES (2) | NO |
| Vitamin B12 deficiency (corpus) | YES | NO |
| Calcium, zinc and iron deficiency (corpus) | YES (7) | NO |
| Peptic ulcer disease (antrum) | YES (3) | NO |
| The risks of the complications of GERD | | |
| Esophagitis and Barrett's esophagus | YES (4) | NO |
| If necessary, a recommendation for | | |
| Gastroscopy and biopsy examination | YES | NO |
| Treatment of H. pylori infection | YES (8) | NOT RELIABLE (1) |
| Determination of vitamin B12 and homocysteine | YES | NO |
| | YES | NO |
| Determination of calcium and iron | | |
| Follow-up examination to monitor | | |
| the incidence of atrophic gastritis | YES (5) | NO |
| the healing of the H. pylori infection | YES | NOT RELIABLE (1) |
| the healing of atrophic gastritis | YES | NO |

(1) The $^{13}$C-urea breath—and stool antigen tests give 40-50% false negative results if the patient has a) atrophic gastritis and related risks, b) MALT lymphoma or c) bleeding peptic ulcer disease or d) if the patient is currently receiving antibiotics or PPIs (proton pump inhibitors). The GastroPanel® H. pylori IgA & IgG antibody test combination does not have these types of false negative results.

(2) The risk of gastric cancer is very low without atrophic gastritis in corpus, antrum or both. But in some cases, a H. pylori infection without histologically observable atrophic gastritis may be associated with gastric cancer and peptic ulcer disease.

(3) No peptic ulcer disease with corpus atrophy (no acid, no ulcer). The risk of peptic ulcer disease is very low without antrum atrophy.

(4) Normal (30-160 μg/l) or high pepsinogen I and/or pepsinogen I and pepsinogen II ratio in association with low gastrin-17 (below 1.0 pmol/l) may indicate high acid (HCl) output and risks for the complications of gastroesophageal reflux disease (GERD).

(5) When the incidence of H. pylori-related atrophic gastritis is monitored, the patient can be offered targeted, safe treatment at the right time. The need for medication and the costs and adverse effects of medication can thus be reduced. If the patient has been diagnosed with peptic ulcer disease (gastric or duodenal ulcer), the H. pylori infection has to be treated (6). It should also be treated if the patient has atrophic gastritis. The patient and the doctor may also agree on eradication treatment for other reasons for example when the patient's close relatives have been diagnosed with gastric cancer.

(6) Press Release: The 2005 Nobel Prize in Physiology or Medicine, 3 Oct. 2005 jointly to Barry Marshall and J. Robin Warren for their discovery of "the bacterium Helicobacter pylori and its role in gastritis and peptic ulcer disease":—"An indiscriminate use of antibiotics to eradicate Helicobacter pylori also from healthy carriers would lead to severe problems with bacterial resistance against these important drugs. Therefore, treatment against Helicobacter pylori should be used restrictively in patients without documented gastric or duodenal ulcer disease." http://nobelprize.org/medicine/laureates/2005/press.html (7) Adequate absorption of dietary calcium requires normal acid secretion that is impaired in atrophic gastritis and in long term PPI therapy. Subsequently, calcium is not absorbed normally in the gut, and the subjects are at risk for osteoporosis and hip fracture. Hypochlorhydric states such as atrophic gastritis and partial gastrectomy have long been known to cause iron deficiency anemia.

(8) Pepsinogen II level below 10-15 μg/l two months after the treatment indicates that the H. pylori eradication is succeeded. Increased level of pepsinogen II (over 10 μg/l) indicates active H. pylori gastritis or inflammation due to the use of non-steroidal anti-inflammatory drugs (e.g. aspirin) or strong alcohol. Dig. Liver Dis. 2005 July; 37(7):501-8. Epub 2005 Apr. 18.

Conclusions on the Use of GastroPanel® in the Evaluation of Gastric Cancer Risk.

The detection of G-17 and subsequent early diagnosis of atrophic gastritis of the antrum provides possibilities to find patients at significant risk for gastric cancer in the gastric antrum, and offers tools to delineate subjects at particular risk for peptic ulcer diseases. It is also important that the diagnosis of atrophic gastritis, limited to gastric corpus (low PGI and low PG I/PG II), is confirmed by the high G-17. This is due to the physiological feedback mechanism between the corpus and antrum, where lack of PGI and the consequent lack of acid secretion results in increase of G-17 production and secretion. On the other hand, low plasma level of G-17 with low PGI (and/or low PGI/PGII ratio) enable to delineate patients at highest risk for gastric cancer; i.e., those with extended and severe atrophic gastritis in both antrum and corpus. These and some other facts below demonstrate how extremely important is the use of the validated combination of PG I and PG II with G-17 and *H. pylori* IgA&IgG antibodies (The GastroPanel® innovation).

Tests Comprised for Example in GastroPanel® abd GastroView™ Combined with Autoantibody Tests.

When performing GastroPanel® together/after/before with additional tests, such as autoantibodies to the parietal cells and/or intrinsic factor as well as antibodies or any other biomarkers to any other autoimmune diseases, these tests (GastroPanel® and an autoimmune biomarker or with an autoimmune biomarker panel) serve as confirmation of each others' results in case of autoimmunity, and help decide a strategy for further characterization of the condition to select the best treatment scheme. The biomarker combination (the panel), with or without the diagnosis of *Helicobacter pylori*, of the PG I, PG II and gastrin-17 biomarkers with one biomarker or several biomarkers of the any autoimmune disease reveals the risk of stomach cancer or precancerous lesions or early cancer. In addition, these combinations (panels) reveals autoimmune diseases or their risks including even asymptomatic and inoperable gastric cancer could be revealed, for example, in autoimmune disease.

Usefulness of GastroPanel® for Screening of Atrophic Gastritis Patients with Autoimmune Thyroid Diseases Corpus restricted atrophic gastritis seems to be associated with autoimmune thyroiditis as well as other autoimmunity processes. Conversely, patients with autoimmune thyroiditis seem to be affected by corpus atrophic gastritis and, in turn, be at risk of gastric neoplasms. A work aimed to explore gastric mucosa status with GastroPanel® in a cohort of 61 patients with Graves or Hashimoto diseases, demonstrated that about twenty percent of the patients presented a serological pattern suggestive of corpus atrophic gastritis. Of the patients 18% had atrophy, 25% had gastritis and 57% were normal. In patients having atrophy: PGI <25 µg/L, G-17>15 pmol/L. Patients having gastritis: PGII>10 µg/L, IgG-Hp>42 U/L. Normal patients: 25<PGI>100 µg/L, PGII<10 µg/L, 2.5<G-17>7.5 pmol/L, IgG-Hp<44 U/L. A very high percentage had corpus atrophic gastritis, if compared to the general population. Upper GI endoscopy with biopsies confirmed in 90% of the patients with low PGI levels the diagnosis of atrophic gastritis. These results suggest to screen with GastroPanel® with all patients with autoimmune thyroiditis.

The invention is now described by means of further illustrative examples.

EXAMPLES

Example 1

The aims of this Example were the following:
1. To evaluate by means of a non invasive test (GastroPanel®) both morphological and functional features of the gastric mucosa in patients affected by autoimmune thyroid diseases;
2. To study the rule of autoimmunity by means of the levels of specific antibodies against the parietal cells and components of thyroid (thyreoglobulin and/or peroxidase) in determining the damage of gastric mucosa.
3. To assess the role of multiple autoimmune diseases in the patofysiology of the atrophic gastritis in such patients.
4. To evaluate symptoms related with the upper part of the digestive system in subjects with autoimmune thyroid disease.

The study population consisted of 159 consecutive patients affected by autoimmune thyroid disease, enrolled from the endocrinological unit of Parma University, Italy. Thyroid function was evaluated by means of thyroid ultrasonography and the dosage of the thyroid hormones FT3, FT4, TSH and antithyroid antibodies (Ab-Tg, Ab-TPO, Ab-TSH-R). The morphology and function of the stomach was assessed using GastroPanel® and a search for antibodies against antiparietal cells in patients with serological diagnosis of atrophic gastritis, and upper gastrointestinal endoscopy was performed with 5 biopsies (2 at the body, 1 at the angulus and 2 in the antrum) according with the Sidney system. Finally, all patients were asked about any experienced upper gastrointestinal symptoms by using a dedicate questionnaire.

The great majority of the subjects were female (141 out of 159), in accordance with the deep involvement of autoimmune thyroiditis in the female sex. The mean age of the patients was 57, ranging from 44 to 67 years. Regarding the functional status of thyroide in such patients the great majority, 72%, showed a clinical picture Hashimoto's disease, opposite to 28% with temporary hyper function (Graves' disease).

Results:

The GastroPanel® data gave mainly low levels of PG1 (less than 25) and high levels of G17 (more than 9), indicating atrophic body gastritis. More precisely, 16% of the patients were found to suffer from atrophic gastritis, out of which 62% was found to be atrophic body gastritis and 38% atrophic pan gastritis. Additionally in 18% of the subjects, non atrophic gastritis was found, which possibly was related to a *Helicobacter pylori* infection. In all patients the diagnosis previously assigned by serology was confirmed by means of upper gastrointestinal endoscopy plus biopsies (5 samples according with the Sidney classification).

One of the problems in singling out patients with atrophic gastritis is the lack of symptoms in such subjects. In fact, generally, only a minority of the examined subjects show a score of symptoms over the cut off value of the global symptom scale, irrespective of the state of the gastric mucosa (normal gastric mucosa, non atrophic gastritis or atrophic gastritis).

Further, in a majority of the examined subjects (80%) the antibodies against parietal cells (APCA) are absent. There is a relationship between the presence of these antibodies and alterations in the gastric mucosa, according to the GastroPanel® results. When the presence of atrophic gastritis in the mucosa is considered, 68% of the patients show a presence of these antibodies, opposite to 8% in non atrophic gastritis, with a very high statistical significance (p<0.0001). On the other hand, when patients with atrophic body gastritis are considered, 93% of APCA positivity is found, opposite to 7% in atrophic pan gastritis (p=0.0002). These results strongly support the close relationship from etiological point of view between the presence of antibodies against the parietal cells and damage in the mucosa.

However, there is a scarce role of *Helicobacter pylori* infections in the determination of the damage in the gastric mucosa. In the slide we recognize the role of H.P. in subjects affected by autoimmune thyroiditis. As expected, only 18% of the examined subjects were affected by an *H. pylori* infection and less than half of such patients (46%) suffered from atrophic gastritis. These results support the autoimmunity as a major mechanism of the damage in this field.

Autoimmunity is a complex phenomenon possibly involving biologically different organs. This means that in same patient it is possible to find, besides thyroid autoimmunity, for example celiac disease, diabetes, dermatological pathologies, such as vitiligo, and of course atrophic body gastritis. In the great majority of the samples analyzed in this example, thyroid autoimmunity was isolated. Further, in 16% of the samples, this autoimmunity was associated with at least one different localization, and in 2% of the subjects three or more autoimmune diseases were found. More interestingly, an inverse relationship is present between atrophic gastritis and the number of autoimmune diseases in the same subject. In fact, when only autoimmune thyroiditis is found in the patients, 15% of the subjects experience atrophic gastritis, opposite to 20% in the group having at least 2 autoimmune diseases, and 50% in the group showing the presence of three or more autoimmune disorders.

When measuring the level of thyroid autoimmunity by using the levels of antibodies against Tg (thyroglobulin) or TPO (thyroid peroxidase), based on a cut off value of 100 mU/L, 96% of the subjects were found to have atrophic gastritis in the group showing a high thyroid autoimmunity, supporting strongly the crucial role of autoimmunity in determining the damage in the body of the stomach.

Conclusions:

The found conclusions of the results of this Example are that:
1. a close relationship between autoimmune thyroid diseases and atrophic gastritis has been established, namely 16% of patients having autoimmune thyroid diseases are prone to develop chronic atrophic gastritis,
2. the autoimmune mechanism for the common damage at the thyroid and the stomach is supported by a statistically significant relationship between both antibodies against parietal cells and high thyroid autoimmunity,
3. it is significant, from a clinical point of view, that patients with proven atrophic body gastritis experience only a few upper gastrointestinal symptoms, suggesting the opportunity to use a non invasive test, such as GastroPanel®, to screen for patients that are candidates for gastroscopy,
4. patients with multiple autoimmune diseases (e.g. thyroiditis, celiac disease, vitiligo, diabetes) are more prone to develop body A.G. (Corpus Atrophic Gastritis).

Example 2

The aims of this Example were the following:

To evaluate the patterns and grading of atrophic chronic gastritis.

To evaluate serum levels of pepsinogen I(PGI) and II (PGII), gastrin and *H. pylori* antibodies. (GastroPanel® Test)

To evaluate the correlation between the values of serum biomarker tests (GastroPanel®) and endoscopic diagnosis of atrophic chronic gastritis.

The study population consisted of 90 patients, out of which 54 were affected by antrum atrophic gastritis, 21 were affected by corpus atrophic gastritis and 15 were affected by atrophic pan gastritis. The antrum atrophic gastritis patients had a mean age of 56 years, and consisted of 29 female patients and 25 male patients. The corpus atrophic gastritis patients had a mean age of 58 years, and consisted of 11 female patients opposite to 10 males. The atrophic pan gastritis patients had the highest mean age (73 years), and consisted of 9 female patients and 6 males. 72% of all patients tested positive for a *H. pylori* infection.

As in Example 1, the GastroPanel® was used to analyze samples from the patients. Further, ELISA tests were performed, and upper gastrointestinal endoscopy was performed with 5 biopsies (2 at the body, 1 at the angulus and 2 in the antrum) according with the Sidney system. Particularly, the samples of the patients were tested for the levels of Pepsinogen I and II (PGI and PGII) as well as Gastrin-17 (G-17).

According to the so-called Correa's Cascade (described by Correa P. et al. in Lancet 1975; 2; 58-60), the development of atrophic gastritis may follow the route of:

Normal gastric mucosa-chronic gastritis-atrophic gastritis-intestinal metaplasia-dysplasia-adenocarcinoma More precisely, corpus atrophic gastritis may develop further into gastric adenocarcinoma, while antrum atrophic gastritis may develop into DU (undifferentiated) lymphoma or MALT (mucosa-associated lymphoid tissue) lymphoma, and atrophic pan gastritis may develop into a gastric ulcer or gastric adenocarcinoma.

The risk factors for developing for example corpus atrophic gastritis or antrum atrophic gastritis include a high age (>60 years), cancer history, FANS, coffee intake, alcohol intake and smoking. For corpus atrophic gastritis, the alcohol and coffee intake play the largest role (the alcohol playing the largest role), while the situation is somewhat different for antrum atrophic gastritis, with coffee intake causing the highest risk, followed by the age of the subject, and only thereafter by alcohol intake.

Results:

For corpus atrophic gastritis, the atrophy is generally graded according to the Sydney system, into the grades 0, 1, 2 and 3. When comparing this grading with the levels of PG-I (Spearman's correlation test), the results obtained were the ones shown below in Table 2.

TABLE 2

| | Grading of atrophy | | | |
|---|---|---|---|---|
| | 0 | 1 | 2 | 3 |
| PG-I | 23 | 37 | 27 | 30 |
| Median | 28-69 | 25-48 | 12-53 | 13-59 |

$p = 0.006$

The Gastrin levels were also measured, with the results giving p=0.047 for gastrin-17 of patients with antrum atrophic gastritis, and p=0.01 for patients with atrophic pangastritis. The levels of total Gastrin were not reliable.

Conclusions:

The conclusions drawn from this Example are that:
PGI levels tend to decrease as the grading of corpus atrophic gastritis increases, while the G-17 values increase,
gastrin-17 seems to be a more reliable marker for the antrum atrophic gastritis than the total gastrin itself, with the G-17 values decreasing as the grading increases.
both the levels of PGI and G-17 decrease in atrophic pan-gastritis.

REFERENCES (1) http://nobelprize.org/medicine/laureates/2005/press.html
(2) http://www.yourhealthbase.com/database/rulcer_drugs.htm
(3) http://www.gastropanel.net
(4) http://www.gastroview.com
(5) http://www.gastroprofile.com
(6) Borch K, Axelsson K, Halgreen H, Damkjaer Nielsen M, Ledin T, Szesci P B. The ratio of Pepsinogen A to Pepsinogen C: A sensitive Test for Atrophic Gastritis. Scan J Gastroenterol 1989: 24: 870-876.

(7) Dinis-Ribeiro M, da Costa-Pereira A, Lopes C, Barbosa J, Guilherme M, Moreira-Dias L, Lomba-Viana H, Silva R, Abreu N, Lomba-Viana R. Validity of Serum Pepsinogen I/II Ratio for the Diagnosis of Gastric Epithelial Dysplasia and Intestinal Metaplasia during the Follow-Up of Patients at Risk for Intestinal-Type Gastric Adenocarcinoma. Neoplasia 2004; 6(5); 449-456.

(8) Germana B, Di Mario F, Cavallaro L G, Moussa A M, Lecis P, Liatoupolou S, Comparato G, Carloni C, Bertiato G, Battiestel M, Papa N, Aragona G, Cavestro G M, Iori V, Merli R, Bertolini S, Caruana P, Franze A. Clinical usefulness of serum pepsinogens I and II, gastrin-17 and anti-*Helicobacter pylori* antibodies in the management of dyspeptic patients in primary care. Digestive and Liver Disease 2005; 3:501-8.

(9) Karnes W E, Samloff I M, Siurala M, Kekki M, Sipponen P, Kim S W R, Walsh J H. Positive Serum Antibody and Negative Tissue Staining for *Helicobacter pylori* in Subjects with Atrophic Body Gastritis. Gastroenterology 1992; 101; 167-174.

(10) Sipponen P, Graham D Y. Importance of atrophic gastritis in diagnostics and prevention of gastric cancer: application of plasma biomarkers. Scand. J. Gstroenterol. 2007; 42 (1); 2-10.

(11) Vans K, Sipponen P, Laxén F, Samloff M, Huttunen J K, Taylor P R, Heinonen O P, Albanes D, Sande N, Virtamo J, Härkönen M & the Helsinki Gastritis Study Group. Implications of Serum Pepsinogen I in Early Endoscopic Diagnosis of Gastric Cancer and Dysplasia. Scan J Gastroenterol 2000; 35; 950-956.

(12) Di Mario F, Franze A, Cavallaro L G. Non-Invasive Diagnosis for Gastric Diseases. One Global Medicine s.r.l 2004; 1-48, www.biohit.com/Literature/Dignostics; 2004 Books

(13) DiMario F, Cavallaro L G, Liatopoulou A, et al. Accuracy of "serological gastric biopsy" in a cohort dyspetic patients, Poster presentation at the DDW 2005, May 15-18, in Chigago, Ill., USA

(14) http://www.google.com/search: "Osmo Suovaniemi vertical measurement principle" and "the King of Patents Osmo Suovaniemi in Finland 2002"

(15) Nurgalieva Z, El-Zimaity H, Graham D, et al. Gastric atrophyt in North America: Histology vs. Non-invasive testing, Poster presentation at the DDW 2005, May 15-18, in Chigago, Ill., USA

(16) Pasechnikov V D, Chukov S Z, Kotelevets S M, et al. Invasive and non-invasive diagnosis of *Helicobacter pylori*-associated atrophic gastritis: A comparative study, Scand J Gastroenterol 2005; 40; 297-301

(17) Sipponen P, Ranta P, Helske T, et al. Serum Levels of Amidated Gastrin-17 and Pepsino gen I in Atrophic Gastritis: An Observation Case-Control Study, Scand J Gastroenterol 2002 (7); 785

(18) Sipponen P, Laxen F, Huotari K, et al. Prevalence of Low Vitamin B12 and High Homocysteine in Serum in an Elderly Male Population: Association with Atrophic Gastritis and *Helicobacter pylori* infection, Scand J Gastroenterol 2003; 12; 1209-14

(19) Sipponen P, Vauhkonen M, Helske T, et al. Patients with Barrett's esophagus show low circulating levels of gastrin-17, *World J Gastroenterol* 2005; 11(38); 5988-5992

(20) Uemura N, Okamoto S, Yamamoto S, et al. *Helicobacter pylori* infection and the development of gastrici cancer, N Eng J Med 2001; 345; 784-789

(21) Vans K, Sipponen P, Laxen F et al. the Helsinki Gastritis Study Group, Implications of serum pepsinogen I in early endoscopic diagnosis of gastric cancer and dysplasia, Scand J Gastroenterol 2000; 9; 950-956

(22) Väänänen H, Vauhkonen M, Helske T, et al Non-Endoscopic Diagnosis of Atrophic Gastritis with a Blood Test. Correlation between Gastric Histology and Serum Levels of Gastrin-17 and Pepsinogen I. A Multicenter Study. Eur J Gastroenterol Hepatol 2003; 15; 885-891

(23) Zagari R M, Nicolini G, Casanova S, et al Diagnosis of atrophic gastritis in the general population based upon a combination of three non invasive tests, Gut 2002; 51 (suppl 11); A39.

(24) http://www.biohit.com/Diagnostics/Service Laboratory

(25) Väkeväinen, S., Tillonen, J., Agarwal, D., Srivastava, N. & Salaspuro, M.: High salivary acetaldehyde after a moderate dose of alcohol in ALDH2-deficient subjects: strong evidence for the local carcinogenic action of acetaldehyde. Alcohol. Clin. Exp. Res. 2000; 25; 873-877

(26) Vakeväinen, S., Tillonen, J., Salaspuro, M., Jousimies-Somer, H., Nuutinen, H., Färkkilä, M. Hypochlorhydria induced by a proton pump inhibitor leads to intragastric microbial production of acetaldehyde from ethanol. Aliment. Pharmacol. Ther 2000; 14; 1511-1518

(27) Väkeväinen, S., Mentula, S., Nuutinen, H., Salmela, K., Jousimies-Somer, H., Färkkilä, M. & Salaspuro, M. et al. Ethanol-derived microbial production of carcinogenic acetaldehyde in achlorhydric atrofic gastritis. Scand. J. Gastroeterol 2002; 37: 648-655

(28) Yang Y X, Lewis J D, Epstein S, et al. Long-term proton pump inhibitor therapy and risk of hip fracture. JAMA 2006; 296; 2947-53

(29) Sharma V R, Brannon M A, Carloss E A. South Med J. 2004 September; 97(9); 887-9

(30) Gatta L, Perna F, Ricci C, et al. Effect of proton pump inhibitors and antacid therapy on $^{13}C$ urea breath test and stool test for *Helicobacter pylori* infection. Am J Gastroenterol 2004; 99:823-829

(31) Graham K S, Graham D Y. Contemporary Diagnosis and Management of *H. pylori*—Associated Gastrointestinal Diseases, Published by Handbooks in Health Care Co, Newtown, Pa., USA, 2002

(32) Graham D Y, Opekun A R, Hammoud F, Yamaoka Y, Reddy R, Osato M S, El-Zimaity H M. Studies regarding the mechanism of false negative urea breath tests with proton pump inhibitors. Am J. Gastroenterol. 2003; 98; 1005-9.

(33) Kokkola A, Rautelin H, Puolakkainen P, et al. Positive result in serology indicates active *Helicobacter pylori* infection in patients with atrophic gastritis. J Clin Microbiol 1998; 36 (6); 1808-10.

(34) Kokkola A, Rautelin H, Puolakkainen P et al. Diagnosis of *Helicobacter pylori*-infection in Patients with Atrophic Gastritis: Comparison of Histology, $^{13}C$ Urea Breath Test, and serology. Scand J Gastroenterol 2000; 25; 138-141

(35) Kokkola A., Rautelin H, Puolakkainen P, Sipponen P, Färkkilä M, Kosunen T U. Diagnosisi of *Helicobacter pylori* infection in Patients with Atrophic Gastritis: Comparison of Histology, 13C Urea Breath Test, and serology. Scand J Gastroenterol 2000; 25; 138-141.

(36) Kokkola A, Rautelin H, Puolakkainen P, Sipponen P, Färkkilä M, Haapiainen R, Kosunen T U. Positive result in serology indicates active *Helicobacter pylori* infection in patients with atrophic gastritis. J Clin Microbiol. 1998; 36 (6) 1808-10

(37) Kosunen T U. Antibody titers in *Helicobacter pylori* infection: implications in the follow-up of antimicrobial therapy. Ann Med 1995; 27:605-607
(38) Jaskowski T D, et al. Immunoglobulin A antibodies to *Helicobacter pylori*. J Clin Microbiol 1997; 35; 2999-3000.
(39) Talley N J, Vakil N, Delaney G, et al. Management issues in dyspepsia: current consensus and controversies. Scand J Gastroenterol 2004; 39 (10); 913-918
(40) Rugge M, Correa P, Dixon M F. et al. Gastric mucosal atrophy: interobserver consistency using new criteria for classification and grading. Aliment Pharmacol Ther 2002; 16; 1-12
(41) Shiotani A, Hiroyasu I, Noriya U, Kumamoto M, Nakae Y, Ishiguro S, Tatsuta M and Graham D. Early Detection and Diagnosis. Histologic and serum risk markers for non-cardia early gastric cancer, Int J Cancer 2005; 115 (3) 463-46
(42) Cao Q, Hua Z and Xiao S D. Screening of atrophic gastritis and gastric cancer by serum pepsinogen, gastrin-17 and *Helicobacter pylori* antibodies. Journal of Digestive Diseases 2007; 8; 15-22.
(43) Winawer S J. New colorectal cancer screening guidelines, BMJ 2003; 327; 196-197.
(44) Toh B et al. Pernicious Anemia. N Eng J Med, 1997; 337: 1441-1448.
(45) Toh B et al. Pernicious Anemia. Autoimmunity, 2004; 37:357-361.
(46) Mardh E et al. Diagnosis of gastritis by means of a combination of serological analyses. Clin Chim Acta 2002; 320:17-27.
(47) Carmel R et al. Prevalence of undiagnosed pernicious anemia in the elderly. Arch Intern Med; 1996; 156:1097-1100.
(48) Chuang J S et al. Diagnostic ELISA for parietal cell autoantibody using tomato lectin-purified gastric H+/K+-ATPase (proton pump). Autoimmunity 1992; 2:1-7.
(49) Goldkorn I et al. Gastric parietal cell antigens of 60-90, 92, and 100-120 kDa associated with autoimmune gastritis and pernicious anemia. Role of N-glycans in the structure and antigenicity of the 60-90-kDa component. J Biol Chem. 1989; 264:18768-74.
(50) Basso N et al. Antigastric autoantibodies in *Helicobacter pylori* infection: role in gastric mucosal inflammation. Int J Clin Lab Res 2000; 30:173-178.
(51) Ching-Chu L et al. Implications of anti-parietal cell antibodies and anti-*Helicobacter pylori* antibodies in histological gastritis and patient outcome World J Gastroenterol 2005; 11:4715-4720
(52) Baxter A G et al. Genetic control of susceptibility to autoimmune gastritis. International Reviews of Immunology, 24: 55-62, 2005.
(53) Uibo R. Contribution of epidemiological studies to gastritis immunology. Int Rev Immunol. 2005; 24:31-54.
(54) Biosafety in Microbiological and Biomedical Laboratories. Centers for Disease Control, National Institutes of Health [HHS Pub. No. (CDC) 93-8395], 1993.
(55) Expert Committee on the Diagnosis and Classification of Diabetes Mellitus. 1997 Report of the expert committee on the diagnosis and classification of diabetes mellitus. Diabetes Care. 20:1183-1197
(56) Eisenbarth G S. 1986 Type 1 diabetes mellitus: a chronic autoimmune disease. N Engl J Med 314:1360-1368.
(57) Cahill Jr G F, McDevitt H O. 1981 Insulin-dependent diabetes mellitus: the initial lesion. N Engl. J. Med. 304: 1454-1465.
(58) Drell D W, Notkins A L. 1987 Multiple immunological abnormalities in patients with type 1 (insulin-dependent) diabetes mellitus. Diabetologia 30:132-143.
(59) Gepts W. 1965 Pathologic anatomy of the pancreas in juvenile diabetes mellitus. Diabetes. 14:619-633.
(60) Botazzo G F, Florin-Christensen A, Doniach D. 1974 Islet-cell antibodies in diabetes mellitus with autoimmune polyendocrine deficiencies. Lancet. 2:1279-1282.
(61) Lernmark A, Freedman Z R, Hofmann C, et al. 1978 Islet-cell-surface antibodies in juvenile diabetes mellitus. N Engl J. Med. 299:375-380.
(62) Palmer J P, Asplin C M, Clemons P, Lyen K, Tatpati O, Raghu P K, et al. 1983 Insulin antibodies in insulin-dependent diabetics before insulin treatment. Science. 222:1337-1339.
(63) Baekkeskov S, Aanstoot H J, Christgau S, et al. 1990 Identification of the 64 kD autoantigen in insulin-dependent diabetes as the GABA-synthesizing enzyme glutamic acid decarboxylase. Nature 374:151-156.
(64) Gorus F K, Goubert P, Semakula C, et al. 1997 IA-2 autoantibodies complement GAD-65 autoantibodies in new-onset IDDM patients can help predict impending diabetes in their siblings. Diabetologia 40:95-99.
(65) Neufeld M, Maclaren N K, Riley W J, et al. 1980 Islet cell and other organspecific antibodies in U.S. Caucasians and Blacks with insulin-dependent diabetes mellitus. Diabetes 29:589-592.
(66) Landin-Olsson M, Karlsson F A, Lernmark A", Sundkvist G, Diabetes Incidence Study in Sweden Group 1992 Islet cell and thyrogastric antibodies in 633 consecutieve 15- to 34-yr-old patients in the Diabetes Incidence Study in Sweden. Diabetes 41:1022-1027.
(67) Bottazzo G F, Cudworth A G, Moul D J, Doniach D, Festenstein H. 1978 Evidence for a primary autoimmune type of diabetes mellitus (type Ib). Br Med J. 2:1253-1255.
(68) Betterle C, Zanette F, Pedini B, et al. 1984 Clinical and subclinical organspecific autoimmune manifestations in type 1 (insulin-dependent) diabetic patients and their first-degree relatives. Diabetologia. 26:431-436.
(69) Riley W J, Winer A, Goldstein D. 1983 Coincident presence of thyro-gastric autoimmunity at onset of type 1 (insulin-dependent) diabetes. Diabetologia. 24:418-421.
(70) Irvine W J, Scarth L, Clarke B F, Cullen D R. 1970 Thyroid and gastric autoimmunity in patients with diabetes mellitus. Lancet. 2:163-168.
(71) Riley W J, Toskes P P, Maclaren N K, Silverstein J. 1982 Predictive value of gastric parietal cell autoantibodies as a marker for gastric and hematologicabnormalities associated with insulin dependent diabetes. Diabetes. 31:1051-1055.
(72) Markson J L, Moore J M. 1962 "Autoimmunity" in pernicious anemia and iron deficiency anemia. Lancet. 2:1240.
(73) Ungar B, Stocks A E, Whittingham S, Martin F I R, Mackay I R. 1968 Intrinsicfactor antibody, parietal-cell antibody, and latent pernicious anemia in diabetes mellitus. Lancet. 2:415-417.
(74) Shearman D J C, Delamore J W, Gardner D L. 1966 Gastric function and structure in iron deficiency anemia. Lancet. 1:845-848.
(75) Kokkonen J. 1980 Parietal cell antibodies and gastric secretion in children with diabetes mellitus. Acta Paediatr Scand. 69:485-489.
(76) De Block C, Van Gaal L, De Leeuw I. 1997 Iron deficiency anemia is associated with gastric autoimmunity in insulindependent diabetic patients (IDDM) [Abstract]. Diabetologia. 40(Suppl 1):A592.

(77) Neufeld M, Maclaren N K, Blizzard R M. 1981 Two types of autoimmune Addison's disease associated with different polyglandular autoimmune (PGA) syndromes. Medicine. 60:355-362.
(78) Karlsson F A, Burman P, Lo"o"f L, Olsson M, Scheynius A, Mardh S. 1987 Enzyme-linked immunosorbent assay of H1/K1-ATPase, the parietal cell antigen. Clin Exp Immunol. 70:604-610.
(79) Van Rood J J, Van Leeuwen A, Ploem J S. 1976 Simultaneous detection of two cell populations by two-colour fluorescence and application to the recognition of B cell determinants. Nature. 262:795-797.
(80) Bodmer J G, Marsh S G E, Parham P, Erlich H A, Albert E, Bodmer W F, et al. 1990 Nomenclature for factors of the HLA system, 1989. Hum Immunol. 28:326-342.
(81) Selam J L, Clot J, Andary M, Mirouze J. 1979 Circulating lymphocyte subpopulations in juvenile insulin-dependent diabetes. Correction of abnormalities by adequate blood glucose control. Diabetologia. 16:35-40.
(82) Vanderkam S G, De Leeuw I H. 1992 Insuline dependente diabetes mellitus in associatie met auto-immuun gei"nduceerde thyreoiditis en gastritis. Tijdschr Geneeskunde. 48:925-928.
(83) Gorsuch A N, Dean B M, Bottazzo G F, Lister J, Cudworth A G. 1980 Evidence that type I diabetes and thyrogastric autoimmunity have different genetic determinants. Br Med J. 280:145-147.
(84) Sachs G, Hersey S J. 1991 The gastric parietal cell, its clinical relevance in the management of acid related diseases. Oxford: Oxford Clinical Communications; 23-32.
(85) Burman P, Mardh S, Norberg L, Karisson F A. 1989 Parietal cell antibodies in pernicious anemia inhibit H1/K1-adenosine triphosphatase, the proton pump of the stomach. Gastroenterology. 96:1434-1438.
(86) Song Y H, Ma J Y, Mardh S, et al. 1994 Localization of a pernicious anemia autoantibody epitope on the a-subunit of the human H,K-adenosine triphosphate. Scand J. Gastroenterol. 29:122-127.
(87) Lam S K, Sircus W. 1976 A comparison of the acid and gastrin secretory responses to hypoglycaemia and meals in duodenal ulcer with and without acid hypersecretion to pentagastrin. Digestion. 14:1-11.
(88) Markievicz K, Lukin M. 1976 Influence of hyperglycaemia on maximal acid secretion in healthy subjects. Digestion. 14:188-191.
(89) Deprez P, Calam J. 1993 Nouveaux me'canismes d'hypergastrine'mie en rapport avec la gastrite atrophique auto-immune et l'infection a' *Helicobacter pylori*. Acta Gastroenterol Belg. 56:245-250.
(90) Ma J Y, Borch K, Sjo"strand E, Janzon L, Mardh S. 1994 Positive correlation between H,K-adenosine triphosphatase autoantibodies and *Helicobacter pylori* antibodies in patients with pernicious anemia. Scand J. Gastroenterol. 29:961-965.
(91) Negrini R., Savio A., Graffeo M., Rolfi F, Ghielmi S. 1993 Auto-antibodies and gastric *Helicobacter pylori* infection: does auto-immuity affect progression to atrophic gastritis? Eur J Gastroenterol Hepatol. 5(Suppl 2):S27-S29.
(92) Uibo R, Vorobjova T, Metskula K, Kisand K, Wadstrom T, Kivik T. 1995 Association of *Helicobacter pylori* and gastric autoimmunity: a populationbased study. FEMS Immunol Med Microbiol. 11:65-68.
(93) Doniach D, Roitt I M. 1964 An evaluation of gastric and thyroid autoimmunity in relation to hematologic disorders. Semin Hematol. 1:313-343.
(94) Karlsson F A, Burman P, Lo"o"f L, Mardh S. 1988 Major parietal cell antigen in autoimmune gastritis with pernicious anemia is the acid-producing H1,K1-adenosine triphosphatase of the stomach. J Clin Invest. 81:475-479.
(95) Davidson R J L, Atrah H I, Sewell H F. 1989 Longitudinal study of circulating gastric antibodies in pernicious anaemia. J Clin Pathol. 42:1092-1095.
(96) Kaplan L M, Graeme-Cook F M. 1997 Case record of the Massachusetts general hospital: a 39 year-old woman with pernicious anemia and a gastric mass. N Engl J. Med. 336:861-867.
(97) Irvine W J. 1975 The association of atrophic gastritis and autoimmune thyroid disease. Clin Endocrinol Metab. 4:351-377.
(98) Dallman P R. 1982 Manifestations of iron deficiency. Semin Hematol. 19:19-30.
(99) Cook J D. 1982 Clinical evaluation of iron deficiency. Semin Hematol. 19:6-18.
(100) Toh B H, Van Driel I R, Gleeson P A. 1997 Mechanisms of disease: pernicious anemia. N Engl J. Med. 337:1441-1448.
(101) Brinton L A, Gridley G, Hrubec Z, Hoover R, Fraumeni Jr J F. 1989 Cancer risk following pernicious anaemia. Br J. Cancer. 59:810-813.
(102) Pokorny G et al. Types of atrophic gastritis in patients with Sjögren's syndrome. Annals of the Rheumatic Diseases 1991; 50: 97-100)
(103) Maury C P J et al. Atrophic gastritis in sjögren's syndrome. Morphologic, biochemical, and immunologic findings. Arthritis and Rheumatism 2005; 28(4): 388-394).
(104) Ishikawa N et al. *Helicobacter pylori* infection in rheumatoid arthritis: effect of drugs on prevalence and correlation with gastroduodenal lesions. Rheumatology 2002; 41: 72-77.
(105) Salonen E M et al. Anti-telomere antibodies in systemic lupus erythematosus (SLE): a comparison with five antinuclear antibody assays in 430 patients with SLE and other rheumatic diseases. Ann Rheum Disease 2004; 63(19: 1250-1254.
(106) Wallace D J et al. Anti-telomere antibodies in systemic lupus erythematosus: a new ELISA test for anti-DNA with potential pathogenic implications.

The invention claimed is:
1. A method for determining the presence of *Helicobacter pylori* infection and/or atrophic gastritis in a person diagnosed as having symptoms of diabetes mellitus type 1, said method comprising the steps of:
   a) obtaining a biological sample from the person diagnosed as having symptoms of diabetes mellitus type 1;
   b) quantitatively measuring a plurality of biomarkers from said biological sample with a non-invasive test(s), wherein said plurality of biomarkers comprises pepsinogen I, pepsinogen II, pepsinogen I/II ratio, gastrin-17 and *Helicobacter pylori* antibodies, and wherein the pepsinogen I, pepsinogen II and gastrin-17 are measured using an antibody;
   c) comparing the values obtained to cut-off values or reference ranges; and
   d) determining that said person diagnosed as having symptoms of diabetes mellitus type 1 has a *Helicobacter pylori* infection and/or atrophic gastritis, based on said comparing.
2. The method according to claim 1, wherein when the pepsinogen I concentration in said sample is close to the lower limit or below the reference range or cut-off value, said person is diagnosed with corpus atrophic gastritis.

3. The method according to claim 1, wherein the reference range for pepsinogen I is 30-160 µg/l; the reference range for pepsinogen II is 3-20 µg/l; the reference range for pepsinogen I/II ratio is 3 or below 3, the reference range for Gastrin-17S (stimulated) is 5-30 pmol/l; the reference range for Gastrin-17B (fasting) is 2-10 pmol/l; and the reference range for HPAB is 0-30 EIU.

4. The method according to claim 1, wherein typical cut-off values for the biomarkers are: pepsinogen I, 30 µg/l; pepsinogen I/II ratio, 3; Gastrin-17S (stimulated), 5 pmol/l; Gastrin-17B (fast), 2 pmol/l; and HPAB, 30 EIU.

5. The method according to claim 1, wherein the biological sample is blood, serum or a plasma sample.

6. A method for determining whether a person having a *Helicobacter pylori* infection and/or atrophic gastritis has diabetes mellitus type I, said method comprising the steps of:
  a) obtaining a biological sample from a person;
  b) quantitatively measuring a plurality of biomarkers from said biological sample with a non-invasive test(s), wherein said plurality of biomarkers comprises pepsinogen I, pepsinogen II, pepsinogen I/II ratio, gastrin-17 and *Helicobacter pylori* antibodies, and wherein the pepsinogen I, pepsinogen II and gastrin-17 are measured using an antibody;
  c) comparing the values obtained to cut-off values or reference ranges, and determining that said person has a *Helicobacter pylori* infection and/or atrophic gastritis based on said comparing;
  d) examining said person for the presence of symptoms indicative of diabetes mellitus type I when said person is determined to have a *Helicobacter pylori* infection and/or atrophic gastritis; and
  e) determining that said person has diabetes mellitus type I when said person has symptoms indicative of diabetes mellitus type I.

7. The method according to claim 6, wherein the biological sample is blood, serum or a plasma sample.

8. The method according to claim 1, wherein the *Helicobacter pylori* antibodies are selected from IgG and IgA antibodies.

9. The method according to claim 6, wherein the *Helicobacter pylori* antibodies are selected from IgG and IgA antibodies.

10. The method according to claim 1, wherein the level of Gastrin-17 is measured separately from measuring the levels of pepsinogen I and pepsinogen II.

11. The method according to claim 6, wherein the level of Gastrin-17 is measured separately from measuring the levels of pepsinogen I and pepsinogen II.

12. The method according to claim 1, wherein when the pepsinogen I concentration in said sample is close to the lower limit or below the reference range or cut-off value; the pepsinogen I/II ratio is close to the lower limit or below the reference range or cut-off value; and the gastrin-17 concentration is close to the upper limit or above the reference range, said person is diagnosed with corpus atrophic gastritis.

* * * * *